United States Patent [19]

Rigdon et al.

[11] 4,089,689
[45] May 16, 1978

[54] PETROLEUM OXIDATE AND CALCIUM DERIVATIVES THEREOF

[75] Inventors: Orville W. Rigdon, Groves; Anthony Macaluso, Sr., Port Arthur, both of Tex.

[73] Assignee: Texaco Inc., New York, N.Y.

[21] Appl. No.: 592,954

[22] Filed: Jul. 3, 1975

[51] Int. Cl.$^2$ ................................................ C09D 5/08
[52] U.S. Cl. ................................ 106/14.28; 106/285; 208/3; 208/14; 252/39; 252/55; 252/396
[58] Field of Search ................... 106/1 A, 285; 208/3, 208/14; 260/451; 252/55, 396, 39

[56] References Cited

U.S. PATENT DOCUMENTS

| | | | |
|---|---|---|---|
| 2,705,241 | 3/1955 | McKinley et al. | 260/451 |
| 2,779,737 | 1/1957 | Koft et al. | 252/39 |
| 2,982,728 | 5/1961 | Whitney | 252/39 |

Primary Examiner—Lorenzo B. Hayes
Attorney, Agent, or Firm—Thomas H. Whaley; Carl G. Ries; Robert A. Kulason

[57] ABSTRACT

A petroleum oxidate of gel resistant properties characterized by a Neut. No. between about 40 and 50, a Sap. No. between about 85 and 105, a specific gravity between about 0.99 and 1.03, a viscosity (SUS at 210° F.) of between about 1200 and 2500 and a melting point of between about 85° and 115° F.; a calcium soap thereof having a calcium content of between about 1.2 and 1.9 wt. % and a melting point between about 155° and 230° F. of gel resistant properties under cutback conditions; said oxidate, calcium soap and cutback thereof respectively prepared by contacting a deasphalted naphthene base residual oil having a molecular weight of between about 300 and 900, a saturate content between about 40 and 60 wt. %, an aromatic content between about 60 and 40 wt. %, a methylene to methyl group mole ratio of between about 1:1 and 2.5:1, and an SUS viscosity (210° F.) of between about 150 and 170, with air at an air rate of between about 5 and 40 SCFH/lb. residual oil charge in the presence of between about 0.2 and 2 lbs. metaliferous oxidation catalyst per pound charge oil under a pressure of between about 0 and 500 atmospheres at a temperature between about 250° and 400° F. for a period of normally between about 1 and 5 hours to form said petroleum oxidate which is then further reacted with calcium hydroxide in a hydroxide amount of between about 100 and 125 wt. % of stoichiometric at a temperature of between about 275° and 357° F. and cutting back the formed calcium soap with inert petroleum hydrocarbon solvent to form a cutback calcium oxidate soap composition containing between 0.1 and 90 wt. % of said oxidate soap of corrosion inhibiting and anti gel properties.

9 Claims, No Drawings

PETROLEUM OXIDATE AND CALCIUM DERIVATIVES THEREOF

BACKGROUND OF INVENTION

The broad class of petroleum oxidates and their calcium soap derivatives are well known corrosion preventing additives in petroleum fractions, e.g., lubricating oils, gasoline, diesel oil, kerosene, etc. where the resultant compositions are either utilized as fuels or as protective coatings. The oxidates are a complex mixture of oxygenated compounds comprising acids, alcohols, aldehydes, esters and ketones, the specific chemical compound combination in the oxidates being dependent upon the chemical makeup of the petroleum fraction oxidized and degree of oxidation. Variations in either wall result in a different combination of chemical compounds. Accordingly, since petroleum oxidates defy description by structure or by nomenclature, the resultant oxidates are defined in terms of properties, source material and/or method of manufacture.

One of the major deficiencies of many of the prior art oxidates is that, in their conversion to the calcium soaps, gelation of the soap products occurs, undesirably resulting in an incomplete soap formation and severe handling difficulties in processing equipment. Further, the gel often persists even under cutback (solvent dilution) conditions resulting in a corrosion inhibiting composition which undesirably cannot be uniformly distributed over a surface to be protected. Even in those cases where gel formation does not occur during saponification, the resultant soap will often form gels under cutback conditions which as heretofore stated results in a product of reduced corrosion inhibiting ability.

SUMMARY OF INVENTION

We have discovered and this constitutes our invention a novel petroleum oxidate and calcium derivative thereof which, in addition to offering superior corrosion protection particularly when in the calcium soap form, surprisingly does not undesirably gel during conversion thereof to the calcium soap or result in calcium soaps which gel under cutback conditions.

DETAILED DESCRIPTION OF THE INVENTION

Specifically, these discoveries are the result of a unique combination of a particular petroleum residual oil fraction and degree of oxidation thereof. The first critical element in the combination is the petroleum fraction from which the oxidate and calcium soap are derived. Specifically, the contemplated petroleum fraction is a deasphalted residual oil resulting from the fractionation of a sweet naphthene base crude which is subsequently deasphalted, said oil having an average molecular weight between about 300 and 900, preferably between about 400 and 700, an aliphatic and cycloaliphatic saturate content between about 40 and 60 wt. % and an aromatic content of between 60 and 40 wt. %, a viscosity (SUS at 210° F.) between about 150 and 170, preferably between 155 and 165 and a methylene to methyl group mole ratio of between about 1:1 and 2.5:1, preferably between 1.5:1 and 2.3:1. Hereinbefore and hereinafter the term "sweet" as applied to the crude base stock is intended to denote a sulfur content of less than about 0.5 wt. %.

Oxidation is conducted on the residual oil until a residual oil oxidate is formed having a Neutralization No. (Neut. No.) between about 40 and 50, preferably between 43 and 47, a Saponification No. (Sap. No.) between about 85 and 105, preferably between about 90 and 100, a melting point point between about 85° and 115° F., preferably between 90 and 105° F. and an SUS viscosity at 210° F. between 1200 and 2500, preferably between 1400 and 1800.

In a typical oxidation procedure, there is initially charged to the oxidation reactor, whether it be batch or continuous, the residual oil together with an oil soluble metaliferous oxidation catalyst such as potassium permanganate, manganese stearate, manganese naphthenate and chromium stearate to only mention a few in an amount ranging between about 0.5 and 2 wt. %, preferably between 0.4 and 0.6 wt. %, based on the residual oil charge employed. Potassium permanganate is preferred. The metaliferous catalyst is normally introduced into the oxidation zone as a between about 2 and 6 wt. % aqueous solution and during the induction period during which air is blown through the reactor and the temperature and pressure are raised to initiate oxidation, the water evaporates leaving the catalyst distributed through the oil charge in a uniform manner. The oxidation is initiated and conducted in the temperature range between about 250° and 400° F., preferably between 275° and 325° F. In the oxidation zone the pressure is maintained between atmospheric and 500 psig, preferably between 65 and 100 psig. Air is passed through the residual charge oil in the oxidation zone at a rate of between about 5 and 40 standard cubic feet per hour per pound charge oil (SCFH/lb.), preferably between 10 and 30 SCFH/lb. charge oil.

Oxidation is continued on a given segment of charge oil until the desired Neut. and Sap. Nos. are attained which is normally in a period from 1 to 5 hours, preferably 2 to 4 hours.

At the end of the oxidation period, the formed residual oil oxidate is either discharged to storage or, if desired, can be subjected to a filtration step. Filtration is normally conducted by passing the oxidate in liquid form over a diatomaceous silica precoated vacuum filter with filtration taking place above the solidification point of the residual oil oxidate, normally between about 100° and 200° F.

The conversion of the residual oil petroleum oxidate to its calcium metal soap derivative is accomplished by standard procedures such as contacting the neat oxidate with lime in an inert gas atmosphere, e.g., nitrogen, at a temperature in the range of between about 275° and 325° F., most preferably between about 275° and 300° F. utilizing between about 100 and 125%, preferably between 110 and 120%, of the lime reactant basis stoichiometric amount required to complete neutralization to form a calcium oxidate soap of a calcium content of between about 1.2 and 1.9 wt. %, preferably between 1.4 and 1.7 wt. %. By the term stoichiometric amount of lime it is intended to mean the quantity which will fully neutralize the oxidate, i.e., to a neutralization number of essentially zero. When a stoichiometric excess of lime is employed, the excess lime remains in the final oxidate product in a solubilized condition and supplements the corrosion inhibiting action of the calcium oxidate soap. Neutralization normally is conducted under conditions of agitation. When neutralization reaction is complete the hot oxidate soap is cut back with any inert hydrocarbon liquid solvent normally having a boiling point between about 220° and 520° F., preferably between 280° and 250° F., such as kerosene, Stoddard solvent, and aromatic and aliphatic naphthenes and mineral spirits boiling with the designated range until the finished cutback concentration is approximately between about 0.1 and 90 wt. %, preferably between 30 and 70 wt. % calcium oxidate soap. The concentrate of the cutback suitable for storage and transport, can have an oxidate content between about 10 and 80 wt. %.

The resultant finished cutback compositions are particularly useful as protective coating form metal surfaces such as auto frames against corrosion. In addition, they do not undesirably gel during the dilution of the metal oxidate soap with cutback solvent or thereafter upon cooling of the cutback composition.

The following examples illustrate the invention but are not to be considered as limitations thereof.

EXAMPLE I

This example illustrates the preparation of the petroleum oxidates of the invention and also the preparation of comparative oxidates. Base Oil A, described below, is the representative deasphalted residual oil derived from a sweet naphthene base crude oil and Base Oils B and C are respectively deasphalted paraffinic residual oil and residuum thereof with Base Oil B being also solvent dewaxed. The properties of the employed base oils are as follows:

TABLE 1

| Description | Base Oil A | Base Oil B | Base Oil C |
|---|---|---|---|
| Gravity, API | 22.9 | 20.2 | 22.5 |
| Flash, COC ° F. | 560 | 600+ | 640 |
| Visc., SUS-210° F. | 156.7 | 276 | 620 |
| Color, Visual | Green | Green | — |
| Pour, ° F. | 45 | 25 | 95 |
| Conradson Carbon, wt. % | 0.83 | 2.2 | 2.3 |
| Sulfur, wt. % | 0.27 | 0.42 | 0.4 |
| Average Mol. wt. | 550 | — | — |
| Methylene/Methyl Group Mole Ratio | 1.9 | — | — |
| Hydrocarbon Saturate Content, wt. % | 52 | — | — |
| Aromatic Hydrocarbon Content, wt. % | 48 | — | — |

In three separate runs, the aforedescribed Base Oils A, B and C were charged to a 30 gallon stainless steel reactor. There also was charged an aqueous solution of potassium permanganate. The reaction mixture was heated to a reaction initiation temperature by heat exchange. After initiation, the reaction mass temperature was rapidly reduced to the operating (reaction) temperature. During the induction period the reaction and air rate were adjusted and during the reaction (oxidation) period the low molecular weight fractions were entrained in the exit gases and were not included in yield calculations. At the end of the reaction period, the reaction mass was rapidly cooled to below 150° F. with the termination of the air introduction followed by analysis of the product. The reaction data and tests on oxidate products were recorded in Table 2:

TABLE 2

| Run No. | 1 | 2 | 3 |
|---|---|---|---|
| Charge Stocks, Wt. Lbs.: | | | |
| A | 100 | — | — |
| B | — | 100 | — |
| C | — | — | 100 |
| Potassium Permanganate | 0.4 | 1.2 | 1.0 |
| Water | 8.7 | 26.0 | 21.7 |
| Reaction Conditions: | | | |
| Initiation Temp., ° F. | 350 | 350 | 350 |
| Reaction Temp., ° F. | 300 | 300 | 300 |

TABLE 2-continued

| Run No. | 1 | 2 | 3 |
|---|---|---|---|
| Reaction Time, Hrs. | 6.25 | 10.92 | 9.34 |
| Air Rate, SCFH | 2660 | 2660 | 2660 |
| Reaction Pressure, psig | 65 | 65 | 65 |
| Products, Wt. Lbs: | | | |
| Oxidate Product | 89.5 | 72.0 | 75 (Est.) |
| Overheads | 22.0 | 36.1 | — |
| Oxidate Product Yield, Wt. % | | | |
| Basis Resid. Charge | 89.5 | 72.0 | 75 (Est.) |
| Tests on Oxidate Product: | | | |
| Neut. No. | 46.2 | 36.9 | 39.3 |
| Sap. No. | 99.3 | 80.0 | 104.7 |
| Melting Point, ° F. | 106.5 | 186 | 175 |
| Specific Gravity 60/60° F. | 1.0126 | 0.9825 | 0.8274 |
| Flash, COC, ° F. | 450 | 510 | 515 |
| Vis., SUS-210° F. | 2461 | —* | —* |
| Ash, Wt. % | 0.44 | 1.9 | 1.4 |

*Too viscous to test.

EXAMPLE II

This example illustrates the preparation of a representative example of the calcium soap derivatives of the residual oil oxidate contemplated herein. In addition, comparative calcium soaps are produced from oxidates outside the scope of the instant invention and the gelling tendencies of the representative cutback calcium soap compositions are compared with the gelling tendencies of these others.

To a 2 liter 3-necked glass flask encompassed by a heating mantle and fitted with a vented condenser and inert gas inlet tube and stirrer, there was charged 500 grams of the petroleum oxidates prepared in Example I together with calcium hydroxide. The mixture was heated to the reaction temperature with stirring. The passage of nitrogen through the reaction mixture was instituted and the by-product water was continually removed as overhead with the nitrogen purge. The heating, stirring and nitrogen purge were continued until neutralization was essentially complete, that is, water of reaction had ceased to evolve. The formed calcium soap was then cut back with Stoddard Solvent and the resultant mixture was optionally filtered through diatomaceous earth to remove unreacted lime.

The procedure employed for the preparation of representative and comparative calcium oxidate soaps is outlined in Table 3 below:

TABLE 3
OXIDATE CALCIUM SOAP PREPARATION LABORATORY PROCEDURE

| Step | | Time, Hrs. | Temp., ° F. |
|---|---|---|---|
| 1. | Charge the following:<br>a). Oxidate, 500 grams | 0.25 | 150 |
| 2. | Start Stirrer and Blow with Nitrogen | — | 150 |
| 3. | Heat to 300° F. | 1.0 | 150–300 |
| 4. | Charge Calcium Hydroxide (Incremental addition) | 0.5 | 300 |
| 5. | React | 5.0 | 300 |
| 6. | Cut Heat, Charge Stoddard Solvent 500 gram; Increase Stirrer Speed | 0.25 | 300 |
| 7. | Cool and continue stirring until Reaction mixture is dissolved in Stoddard Solvent | 2.5 | 300–200 |
| 8. | Disassemble apparatus and pour out product | 0.25 | 200 or lower |

The charge stocks, operating conditions and product are set forth below in Table 4:

TABLE 4

| Run No. | AA | BB | CC | DD | EE |
|---|---|---|---|---|---|
| Oxidate (Table 2) | 1 | 1 | 1 | 2 | 3 |
| Charge Wts., Grams | | | | | |
| Oxidate | 500 | 500 | 500 | 1500 | 500 |
| Ca (OH)$_2$ | 16.8 | 16.8 | 21.4 | 12.4 | 14.3 |
| % Stoichiometric | 10 | 10 | 40 | 10 | 10 |
| Stoddard Solvent | 500 | 500 | 500 | 500 | 500 |
| Reaction Conditions | | | | | |
| Start Base Add'n, ° F. | 275 | 320 | 275 | 275 | 277 |
| Finish Base Add'n, ° F. | 280 | 321 | 275 | 290 | 275 |
| Duration, Hrs. | 0.5 | 0.5 | 0.5 | 0.5 | 0.5 |
| Holding period, Hrs. | 5 | 5 | 5 | 5 | 5 |
| Temp., ° F. | 257–290 | 317–329 | 275 | 275–290 | 272–278 |
| Solvent Additions, ° F. | 275 | 320 | 275 | 275 | 278 |
| Recovery Wts., g. | | | | | |
| Calcium Soap Cutback | 867 | 1001 | 1000 | 998 | 1000 Est. |
| Water | 1.0 | 4 | 4.5 | — | — |
| Analyses | | | | | |
| Soap Melting Point, ° F. | 131–140 | 176 | 160 | — | — |
| Infrared | Calcium Soap Major | Calcium Soap Major | Calcium Soap Major | Calcium Soap Minor (<1%) | Calcium Soap Minor (<1%) |
| Cutback Characteristics | Mobile liquid | Mobile liquid | Mobile liquid | Hard Gel | Hard Gel |
| Remarks | Did not gel | Did not gel | Did not gel | Gelled during neutralization | Gelled during neutralization |

As can be seen from the above, the cutback calcium oxidate soap composition of representative Runs AA, BB, and CC were mobile liquids and did not gel, whereas in Comparative Run DD and EE a hard gel was formed.

EXAMPLE III

This example illustrates the effectiveness of the cutback calcium oxidate soap compositions of the invention as anticorrosive agents.

A 14 day salt spray test according to military specification MIL-C-16173B Grade 4 was utilized in respect to representative cutback calcium soap compositions AA, BB and CC and comparative cutback calcium oxidate soap compositions DD and EE all described in Table 4 of Example II. The military specification is normally used to determine effectiveness of the calcium oxidate soaps as rust preventatives in the field of automotive framing rust proof materials. Representative compositions AA, BB and CC "Passed" the spray test and comparative compositions DD and EE "Failed" said test.

We claim:

1. An oxidate of a deasphalted residual oil derived from a sweet naphthene base crude, said oxidate having a Neut. No. between about 40 and 50, a Sap. No. between about 85 and 105, a melting point between about 85° and 115° F., and a SUS viscosity at 210° F. of between 1200 and 2500, said residual oil having an SUS viscosity at 210° F. between about 150 and 170, an average molecular weight between about 300 and 900, a hydrocarbon saturate content between about 40 and 60 wt. %, an aromatic hydrocarbon content of between about 60 and 40 wt. % and a methylene to methyl group mole ratio of between about 1:1 and 2.5:1.

2. An oxidate in accordance with claim 1 having a Neut. No. between 43 and 47, a Sap. No. between 90 and 100, a melting point between 90° and 110° F., and an SUS viscosity at 210° F. of between 1400 and 1800, said residual oil having an SUS viscosity at 210° F. between 155 and 165, an average molecular weight between 400 and 700, a hydrocarbon saturate content between 40 and 60 wt. %, an aromatic hydrocarbon content of between 60 and 40 wt. %, and a methylene to methyl group mole ratio of between 1.5:1 and 2.3:1.

3. An oxidate in accordance with claim 1, said oxidate having a Neut. No. of about 46, a Sap. No. of about 99, a melting point of about 107° F., and an SUS viscosity at 210° F. of about 2460, said residual oil having an SUS viscosity at 210° F. of about 157, an average molecular weight of about 550, a hydrocarbon saturate content of about 52 wt. %, an aromatic hydrocarbon content of about 48 wt. % and a methylene to methyl group mole ratio of about 1.9:1.

4. A calcium oxidate soap of antigelling properties having a calcium content of between about 1.2 and 1.9 wt. % prepared by neutralizing a petroleum oxidate with lime utilizing a lime quantity of between about 100 and 125 wt. % of stoichiometric, said petroleum oxidate prepared from a deasphalted residual oil derived from a sweet naphthene base crude, said petroleum oxidate having a Neut. No. between about 40 and 50, a Sap. No. between about 85 and 105, a melting point between about 85° and 115° F., and an SUS viscosity at 210° F. of between about 1200 and 2500, said residual oil having an SUS viscosity at 210° F. between about 150 and 170, an average molecular weight between about 300 and 900, a hydrocarbon saturate content between about 40 and 60 wt. %, an aromatic hydrocarbon content of between about 60 and 40 wt. % and a methylene to methyl mole ratio of between about 1:1 and 2.5:1.

5. A calcium oxidate oxidate soap in accordance with claim 4 having a calcium content of between about about 1.4 to 1.7 wt. % prepared by neutralizing a petroleum oxidate with lime utilizing a lime quantity of between about 110 and 120 wt. % of stoichiometric, said petroleum oxidate prepared from a deasphalted residual oil derived from a sweet naphthene base crude, said petroleum oxidate having a Neut. No. between about 43 and 47, a Sap. No. between about 90 and 100, a melting point between about 90 and 110, and an SUS viscosity at 210° F. of between about 1400 and 1800, said residual oil having an SUS viscosity at 210° F. between about 155 and 165, an average molecular weight between about 400 and 700, a hydrocarbon saturate content between about 40 and 60 wt. %, an aromatic hydrocarbon content of between about 60 and 40 wt. %, and a methylene to methyl mole ratio of between about 1.5:1 and 2.3:1.

6. A calcium oxidate soap in accordance with claim 5 wherein said Neut. No. is about 45, said Sap. No. is about 99, said melting point is about 107, said oxidate SUS viscosity is about 2460, said oil SUS viscosity is about 157, said average molecular weight is about 550, said saturate content is about 52 wt. %, said aromatic hydrocarbon content is about 48 wt. %, and said methylene to methyl mole ratio is about 1.9:1.

7. A liquid cutback composition affording corrosion protection and of antigelling properties comprising:
   (a). between about 0.1 and 90 wt. % of a calcium soap of antigelling properties having a calcium content of between about 1.2 and 1.9 wt. % prepared by neutralizing a petroleum oxidate with lime utilizing a lime quantity of between about 100 and 125 wt. % of stoichiometric, said petroleum oxidate prepared from a deasphalted residual oil derived from a sweet naphthene base crude, said petroleum oxidate having a Neut. No. between about 40 and 50, a Sap. No. between about 85 and 105, a melting point between about 85° and 115° F., and an SUS viscosity at 210° F. of between about 1200 and 2500, said residual oil having an SUS viscosity at 210° F. between about 150 and 170, an average molecular weight between about 300 and 900, a hydrocarbon saturate content between about 40 and 60 wt. %, an aromatic hydrocarbon content of between about 60 and 40 wt. % and a methylene to methyl mole ratio of between about 1:1 and 2.5:1.
   (b). between about 99.9 and 10 wt. % of an inert liquid hydrocarbon solvent of a boiling point between about 220° and 520° F.

8. A liquid cutback composition in accordance with claim 7 comprising:
   (a). between about 20 and 80 wt. % of a calcium oxidate soap of antigelling properties having a calcium content of about 1.4 and 1.7 wt. % prepared by neutralizing a petroleum oxidate with lime utilizing a lime quantity of between about 110 and 120 wt. % of stoichiometric, said petroleum oxidate prepared from a deasphalted residual oil derived from a sweet naphthene base crude, said petroleum oxidate having a Neut. No. between about 43 and 47, a Sap. No. between about 90 and 100, a melting point between about 90 and 110° F. and an SUS viscosity at 210° F. of between about 1400 and 1800, said residual oil having an SUS viscosity at 210° F. between about 155 and 165, an average molecular weight between about 400 and 700, a hydrocarbon saturate content between about 40 and 60 wt. % and a methylene to methyl mole ratio of between about 1.5:1 and 2.3:1.
   (b). between about 80 and 20 wt. % of an inert liquid petroleum distillate of a boiling point between about 280° and 520° F.

9. A composition in accordance with claim 7 wherein said Neut. No. is about 46, said Sap. No. is about 99, said melting point is about 107° F., said oxidate SUS viscosity is about 2460, said oil SUS viscosity is about 157, said average molecular weight is about 550, said hydrocarbon saturate content is about 52 wt. %, said aromatic hydrocarbon content is about 48 wt. %, said methylene to methyl group mole ratio is about 1.9:1, and said petroleum distillate is Stoddard's Solvent.

* * * * *